United States Patent [19]

Darke et al.

[11] Patent Number: 5,486,470
[45] Date of Patent: Jan. 23, 1996

[54] PURIFIED HERPES SIMPLEX VIRUS PROTEASE AND METHODS OF PURIFICATION

[75] Inventors: Paul L. Darke, Blue Bell; Dawn L. Hall, Spring City; Lawrence C. Kuo, Solebury, all of Pa.

[73] Assignee: Merck & Co., Inc., Rahway, N.J.

[21] Appl. No.: 279,754

[22] Filed: Jul. 21, 1994

[51] Int. Cl.$^6$ ............................................. C12N 9/50
[52] U.S. Cl. ..................... 435/219; 435/235.1; 435/815
[58] Field of Search ............................ 435/219, 235.1, 435/815

[56] References Cited

FOREIGN PATENT DOCUMENTS

0514830A2  11/1992  European Pat. Off. .
WO93/01291  1/1993  WIPO .

OTHER PUBLICATIONS

EM Seperations Technology, published by E. Merck, Darmstadt, Germany, 1994, pp. 63–67.
Welch et al., 1993 "Herpes Proteinase: Site-Directed Mutagenesis . . . " J. Virology 67(12): 7360–7372.
Weinheimer et al. 1993 "Autoproteolysis of Herpes Simplex Virus Type I Protesase . . . " J. Virology 67(10): 5813–5822.
DiIanni et al. 1993 "In Vitro Activity of the Herpes Simplex Type I Protease . . . " J. Biol. Chem. 268(34): 25449–25454.

Primary Examiner—Charles L. Patterson, Jr.
Attorney, Agent, or Firm—Joanne M. Giesser; Jack L. Tribble

[57] ABSTRACT

A method of purifying proteases from the Herpes Simplex Virus 1 and 2 is taught. A precursor protease is cloned in a host cell and then separated from the cell culture using cation exchange chromatography. The resulting protease is subjected to autoprocessing conditions and an autolytic cleavage occurs, resulting in mature protease.

17 Claims, 1 Drawing Sheet

```
ATG GCA GCC GAT GCC CCG GGA GAC CGG ATG GAG GAG CCC CTG CCa GAC AGG GCC GTG CCC  60
 M   A   A   D   A   P   G   D   R   M   E   E   P   L   P   D   R   A   V   P   20

ATT TAC GTG GCT GGG TTT TTG GCC CTG TAT GAC AGC GGG GAC TCG GGC GAG TTG GCA TTG 120
 I   Y   V   A   G   F   L   A   L   Y   D   S   G   D   S   G   E   L   A   L   40

GAT CCG GAT ACG GTG CGG GCG GCC CTG CCT CCG GAT AAC CCA CTC CCG ATT AAC GTG GAC 180
 D   P   D   T   V   R   A   A   L   P   P   D   N   P   L   P   I   N   V   D   60

CAC CGC GCT GGC TGC GAG GTG GGG CGG GTG CTG GCC GTG GTC GAC GAC CCC CGC GGG CCG 240
 H   R   A   G   C   E   V   G   R   V   L   A   V   V   D   D   P   R   G   P   80

TTT TTT GTG Gga CTG ATC GCC TGC GTG Caa CTG GAG CGC GTC CTC GAG ACG GCC GCC AGC 300
 F   F   V   G   L   I   A   C   V   Q   L   E   R   V   L   E   T   A   A   S  100

GCT GCG ATT TTC GAG CGC CGC GGG CCG CCG CTC TCC CGG GAG GAG CGC CTG TTG TAC CTG 360
 A   A   I   F   E   R   R   G   P   P   L   S   R   E   E   R   L   L   Y   L  120

ATC ACC AAC TAC CTG CCC TCG GTC TCC CTG GCC ACA AAA CGC CTG GGG GGC GAG GCG CAC 420
 I   T   N   Y   L   P   S   V   S   L   A   T   K   R   L   G   G   E   A   H  140

CCC GAT CGC ACG CTG TTC GCG CAC Gta GCG CTG TGC GCG ATC GGG CGG CGC Ctt GGC ACT 480
 P   D   R   T   L   F   A   H   V   A   L   C   A   I   G   R   R   L   G   T  160

ATC GTt ACC TAC GAC ACC GGT CTC GAC GCC GCC ATC GCG CCC TTT CGC CAC CTG TCG CCG 540
 I   V   T   Y   D   T   G   L   D   A   A   I   A   P   F   R   H   L   S   P  180

GCG TCT CGC GAG GGG GCG CGG CGA CTG GCC GCC GAG GCC GAG CTC GCG Cta TCC Gga CGC 600
 A   S   R   E   G   A   R   R   L   A   A   E   A   E   L   A   L   S   G   R  200

ACC TGG GCG CCC GGC GTG GAG GCG CTG ACC CAC ACG CTG CTT TCC ACC GCC GTT AAC AAC 660
 T   W   A   P   G   V   E   A   L   T   H   T   L   L   S   T   A   V   N   N  220

ATG ATG CTG CGG GAC CGC TGG AGC CTG GTG GCC GAG CGG CGG CGG CAG GCC GGG ATC GCC 720
 M   M   L   R   D   R   W   S   L   V   A   E   R   R   R   Q   A   G   I   A  240

GGA CAC ACC TAC CTC CAG GCG AGC GAA AAA TTC AAA ATG TGG GGG GCG GAG CCT GTT TCC 780
 G   H   T   Y   L   Q   A   S   E   K   F   K   M   W   G   A   E   P   V   S  260

GCG CCG GCG CGC GGG TAT AAG AAC GGG GCC CCG GAG TCC ACG GAC ATA CCG CCC GGC TCG 840
 A   P   A   R   G   Y   K   N   G   A   P   E   S   T   D   I   P   P   G   S  280

ATC GCT GCC GCG CCG CAG GGT GAC CGG TGC CCA ATC GTC CGT CAG CGC GGG GTC GCC TcG 900
 I   A   A   A   P   Q   G   D   R   C   P   I   V   R   Q   R   G   V   A   S  300 cCC CCG GTA CTG CCC CCC                                                         918
 P   P   V   L   P   P                                                          306
```

FIG.1

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 918 base pairs
        ( B ) TYPE: nucleic acid
        ( C ) STRANDEDNESS: double
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

```
ATGGCAGCCG  ATGCCCCGGG  AGACCGGATG  GAGGAGCCCC  TGCCAGACAG  GGCCGTGCCC      60

ATTTACGTGG  CTGGGTTTTT  GGCCCTGTAT  GACAGCGGGG  ACTCGGGCGA  GTTGGCATTG     120

GATCCGGATA  CGGTGCGGGC  GGCCCTGCCT  CCGGATAACC  CACTCCCGAT  TAACGTGGAC     180

CACCGCGCTG  GCTGCGAGGT  GGGGCGGGTG  CTGGCCGTGG  TCGACGACCC  CCGCGGGCCG     240

TTTTTTGTGG  GACTGATCGC  CTGCGTGCAA  CTGGAGCGCG  TCCTCGAGAC  GGCCGCCAGC     300

GCTGCGATTT  TCGAGCGCCG  CGGGCCGCCG  CTCTCCCGGG  AGGAGCGCCT  GTTGTACCTG     360

ATCACCAACT  ACCTGCCCTC  GGTCTCCCTG  GCCACAAAAC  GCCTGGGGGG  CGAGGCGCAC     420

CCCGATCGCA  CGCTGTTCGC  GCACGTAGCG  CTGTGCGCGA  TCGGGCGGC   CCTTGGCACT     480

ATCGTTACCT  ACGACACCGG  TCTCGACGCC  GCCATCGCGC  CCTTTCGCCA  CCTGTCGCCG     540
```

```
GCGTCTCGCG AGGGGGCGCG GCGACTGGCC GCCGAGGCCG AGCTCGCGCT ATCCGGACGC    600

ACCTGGGCGC CCGGCGTGGA GGCGCTGACC CACACGCTGC TTTCCACCGC CGTTAACAAC    660

ATGATGCTGC GGGACCGCTG GAGCCTGGTG GCCGAGCGGC GGCGGCAGGC CGGGATCGCC    720

GGACACACCT ACCTCCAGGC GAGCGAAAAA TTCAAAATGT GGGGGGCGGA GCCTGTTTCC    780

GCGCCGGCGC GCGGGTATAA GAACGGGGCC CCGGAGTCCA CGGACATACC GCCCGGCTCG    840

ATCGCTGCCG CGCCGCAGGG TGACCGGTGC CCAATCGTCC GTCAGCGCGG GGTCGCCTCG    900

CCCCCGGTAC TGCCCCCC                                                  918
```

(2) INFORMATION FOR SEQ ID NO:2:

(i) SEQUENCE CHARACTERISTICS:
       (A) LENGTH: 306 amino acids
       (B) TYPE: amino acid
       (C) STRANDEDNESS: double
       (D) TOPOLOGY: linear (iii) HYPOTHETICAL: NO (iv) ANTI-SENSE: NO (xi) SEQUENCE DESCRIPTION: SEQ ID NO:2:

```
Met  Ala  Ala  Asp  Ala  Pro  Gly  Asp  Arg  Met  Glu  Glu  Pro  Leu  Pro  Asp
  1              5                       10                      15

Arg  Ala  Val  Pro  Ile  Tyr  Val  Ala  Gly  Phe  Leu  Ala  Leu  Tyr  Asp  Ser
                20                      25                      30

Gly  Asp  Ser  Gly  Glu  Leu  Ala  Leu  Asp  Pro  Asp  Thr  Val  Arg  Ala  Ala
            35                      40                  45

Leu  Pro  Pro  Asp  Asn  Pro  Leu  Pro  Ile  Asn  Val  Asp  His  Arg  Ala  Gly
       50                       55                      60

Cys  Glu  Val  Gly  Arg  Val  Leu  Ala  Val  Val  Asp  Asp  Pro  Arg  Gly  Pro
 65                       70                      75                      80

Phe  Phe  Val  Gly  Leu  Ile  Ala  Cys  Val  Gln  Leu  Glu  Arg  Val  Leu  Glu
                    85                      90                      95

Thr  Ala  Ala  Ser  Ala  Ala  Ile  Phe  Glu  Arg  Arg  Gly  Pro  Pro  Leu  Ser
               100                     105                    110

Arg  Glu  Glu  Arg  Leu  Leu  Tyr  Leu  Ile  Thr  Asn  Tyr  Leu  Pro  Ser  Val
           115                     120                    125

Ser  Leu  Ala  Thr  Lys  Arg  Leu  Gly  Gly  Glu  Ala  His  Pro  Asp  Arg  Thr
       130                     135                    140

Leu  Phe  Ala  His  Val  Ala  Leu  Cys  Ala  Ile  Gly  Arg  Arg  Leu  Gly  Thr
145                     150                     155                    160

Ile  Val  Thr  Tyr  Asp  Thr  Gly  Leu  Asp  Ala  Ala  Ile  Ala  Pro  Phe  Arg
                   165                     170                    175

His  Leu  Ser  Pro  Ala  Ser  Arg  Glu  Gly  Ala  Arg  Arg  Leu  Ala  Ala  Glu
               180                     185                    190

Ala  Glu  Leu  Ala  Leu  Ser  Gly  Arg  Thr  Trp  Ala  Pro  Gly  Val  Glu  Ala
           195                     200                    205

Leu  Thr  His  Thr  Leu  Leu  Ser  Thr  Ala  Val  Asn  Asn  Met  Met  Leu  Arg
       210                     215                    220

Asp  Arg  Trp  Ser  Leu  Val  Ala  Glu  Arg  Arg  Arg  Gln  Ala  Gly  Ile  Ala
225                     230                     235                    240

Gly  His  Thr  Tyr  Leu  Gln  Ala  Ser  Glu  Lys  Phe  Lys  Met  Trp  Gly  Ala
                   245                     250                    255

Glu  Pro  Val  Ser  Ala  Pro  Ala  Arg  Gly  Tyr  Lys  Asn  Gly  Ala  Pro  Glu
               260                     265                    270
```

```
       Ser  Thr  Asp  Ile  Pro  Pro  Gly  Ser  Ile  Ala  Ala  Ala  Pro  Gln  Gly  Asp
                 275                      280                          285

Arg  Cys  Pro  Ile  Val  Arg  Gln  Arg  Gly  Val  Ala  Ser  Pro  Pro  Val  Leu
                 290                      295                     300

Pro  Pro
       305
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:3:

```
       His  Thr  Tyr  Leu  Gln  Ala  Ser  Glu  Lys  Phe  Lys  Met
       1                   5                        10
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:4:

```
       Ala  Leu  Val  Asn  Ala  Ser  Ser  Ala  Ala  His  Val  Asp  Val  Asp  Thr  Ala
       1                   5                        10                         15

Arg  Ala  Ala  Asp
                      20
```

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:5:

```
       Arg  His  Leu  Ser  Pro  Ala  Ser  Arg  Glu  Gly  Ala  Arg  Arg  Leu
       1                   5                        10
```

PURIFIED HERPES SIMPLEX VIRUS PROTEASE AND METHODS OF PURIFICATION

This invention is directed to a novel method for purifying herpes simplex viral protease.

BACKGROUND OF THE INVENTION

The Herpes Group of viruses includes many viruses which are pathogenic in humans, such as Herpes Simplex Virus (HSV), Varicella Zoster Virus (VZV), Cytomegalovirus (CMV), and Epstein-Barr Virus (EBV). In this group, B-capsids are essential intermediate structures in virion replication and are formed during the assembly of viral capsids in cell nuclei. One of the more abundant protein components of B capsids, the assembly protein, undergoes proteolytic pressing at its C-terminus and is packaged in mature, infectious virions only in its shortened, mature form (Gibson W. and Roizman, B. 1972. *J. Virology* 10:1044–1052).

For HSV, the assembly protein is designated ICP35. The protease which acts on the assembly protein is encoded in the same open reading frame as the ICP35 assembly protein, designated the $U_L26$ gene (Liu, F. and Roizman, B. 1992 *Proc. Natl. Acad. Sci. USA* 89:2076–2080). The catalytic domain of the protease is contained within the first 247 amino acids of a 635 amino-acid protein and is apparently released from the precursor through cleavage by the HSV protease itself (Weinheimer, S. P. et al., 1993 *J. Virology* 67:5813–5822; Welch, A. R. et al., 1991, *Proc. Natl. Acad. Sci. USA* 88: 10792–10796; Deckman, I. C. et al., 1992, *J. Virol.* 66: 7362–7367).

Protease activity appears to be essential for viral replication within the entire group of herpes viruses. Thus, it would be desirable to characterize the herpes group proteases as potential antiviral targets. However, the herpes viral proteases, in the form of fusion proteins, have only been partially purified. (Dilanni, C. L. et al., 1993, *J. Biolog. Chem.* 268:25449–25454; and Weinheimer, S. P. et al., supra). Other herpes proteases (cmv) have been purified and described (see, e.g. WO 93/01291, published Jan. 21, 1993, Applicant: The Johns Hopkins University).

DETAILED DESCRIPTION OF THE INVENTION

This invention is directed to a method for obtaining isolated and purified herpes simplex viral protease, preferably from the Herpes Simplex 1 or Herpes Simplex 2 Viruses. The method for producing a mature viral protease comprises the steps of separating precursor viral protease from non-protease constituents of a cell culture, and subjecting the precursor protease to autoprocessing conditions so that the precursor protease undergoes autocatalytic cleavage to form mature protease.

In a preferred embodiment of this invention the separation of precursor protein from other cellular components occurs using a cation exchange column. If desired, the mature protease can be separated from the cleavage products by an additional chromatography step. The high purity of the mature protease product of this invention takes advantage of the finding that mature prom and precursor proteases elute differently, so that impurities which co-elute with precursor protease do not co-elute with mature protease.

In one embodiment of this invention the protease is from HSV-1; however due to the sequence homologies between the two vital genes and proteins, this invention applies to both Herpes Simplex Virus 1 and Herpes Simplex Virus 2.

DESCRIPTION OF THE FIGURES

FIG. 1 is the DNA and amino acid sequence for HSV 1 protease (SEQ. ID. NOS.:1 and 2). The amino acids confirmed by peptide sequencing are double-underlined. N-termini of the 32 kDa and 27 kDa proteins were identical, beginning with the Ala in position 2.

DEFINITIONS

As used throughout the specification and claims, the following definitions shall apply:

Protease—When used without the descriptor "precursor" or "mature" refers to either form of protease.

Precursor protease—A protease from a Herpes Simplex 1 or 2 Virus which undergoes autolytic cleavage, producing as one of the cleavage products a mature viral protease.

Mature protease—The active form of viral protease which results from the autocatalytic cleavage of a precursor protease.

Autoprocessing—The autocatalytic cleavage of a precursor protease to produce a mature protease.

Autoprocessing conditions—Any condition which increases the ability of the precursor protein to undergo autocatalytic cleavage.

Substantially similar protease—Protease which has substantially the same proteolytic activity as the proteases of this invention and which is encoded by a DNA which hybridizes to the DNA of FIG. 1 under stringent conditions.

Stringent hybridizing conditions—Any of the hybridization conditions known in the an and so considered. See, for example those described in Maniatis et at., 1982, *Molecular Cloning: A Laboratory Manual,* Cold Spring Harbor Laboratory pages 387–389, hereby incorporated by reference. An example of stringent hybridization conditions is incubation in 4 X SSC at 65° C., followed by washing in 0.1 X SSC.

Purified protease—Viral protease which has a minimum purity of 90% by weight.

To produce the purified mature protease of this invention, the gene for the precursor protease, either from HSV-1 or HSV-2, may be introduced into a host cell. The full length protein encoded by the HSV-1 protease gene has 635 amino acids, but the catalytic activity resides in the first 247 amino acids (the first MET is cleaved off, leaving an active 246-residue mature protease). Therefore, it is not necessary to transform a host cell with the entire DNA which encodes all 625 amino acids. It is only required that the host cell be transformed with a gene fragment which will result in the production of the active portion. One may thus transform a host cell with DNA encoding the first 247 amino acids, or one may transform a host cell with a DNA encoding a longer portion, and allow the protease to exert its autocatalytic ability to convert the longer portion into the active mature protease. In a preferred embodiment, host cells are transformed with a segment which encodes at least 306 amino acids, which can self-cleave.

A preferred host cell is a bacterial host cell such as *Escherichia coli,* but any cell which is capable of producing Herpes Simplex Virus protease, including insect cells may be used. The gene for the precursor protease may be part of a vector system, such as a plasmid or baculovirus, wherein the nucleic acid encoding the precursor protease is under the control of a promoter, and/or other desired regulatory elements such as enhancers or the like. Suitable vectors are well known in the art and there are numerous commercially available vectors. One preferred vector for such expression is pET 3C, described in more detail in the Examples. The protease gene (or gene fragment) is inserted into the vector and the vector is introduced into the host cells using known techniques. The host cells are cultured under conditions suitable to their expression of the introduced gene; such culture conditions are also well known in the art.

In a preferred embodiment, the expression product of the Herpes Simplex Viral 1 protease open reading frame has 306 amino acids, as seen in FIG. 1. However, in host cells such as E. coli, the initial N-formyl methionine is removed, so the first amino acid of the resulting precursor protease begins with amino acid #2. Under appropriate autoprocessing conditions, the precursor protease self-cleaves between amino acid residues 247 and 248 to produce two cleavage products: the mature protease of 246 amino acids and a 59 amino acid fragment.

The 306 amino acid protein depicted in FIG. 1 has an identical amino acid sequence to the first 247 amino acids of the corresponding region of the HSV-1 strain 17 protease (Genebank accession number X14112 locus H21CG). At codons 300 and 301, two nucleotides base changes alter two residues of the expression construct relative to strain 17 (L300S, S301P). However, after autoprocessing (below), these residues are not retained in the mature HSV protease.

The precursor form of the protease is expressed and accumulates in the host cell. In a preferred embodiment, isopropyl-β,D-thiogalactopyranoside (IPTG) may be used to induce protein synthesis from the plasmid-encoded gene, particularly when the transcription of the gene is driven by a T7 promoter. In one embodiment, the expressed precursor protease is 306 amino acids long and has an apparent molecular mass of 32 kDa. Host cells are harvested, and may be lysed. One such way to lyse is treatment with hen egg white lysozyme in pH 7.5 50 mM TRIS HCl, followed by treatment with DNAse. Soluble and insoluble portions of the lysate are separated by centrifugation. While the precursor protease may be found in both the solubilized or non-solubilized fraction, it is preferred to further purify the protease from the soluble fraction in order to avoid the uncertainties encountered when enzymes are exposed to solubilizing agents such as urea or guanidine hydrochloride.

Next, the precursor protein is separated from the non-protease constituents of the host cells culture by cation exchange chromatography. In this step, the soluble fraction is applied to a cation exchange column resin, preferably to a "Fractogel-SO$_3$®" column, commercially available from E. Merck. Fractogel-SO$_3$® is a tentacle cation exchanger consisting of an insoluble matrix, copolymerized from oligoethyleneglycol, glycidylmethacrylate and pentaerythroldimethacrylate, to which are grafted polymerized chains of acrylamide derivatives that are approximately 15 to 50 units in length. Most of the host cell proteins do not adhere to the cation exchange resin, but the precursor and mature forms of the protease do. It was surprising and unexpected that the protease would bind to this cation exchange resin, as the isoelectric points for the precursor and mature forms of the protease enzyme are 6.3 and 5.8, while the pH used in the Fractogel® cation exchange column step is higher than the enzyme isoelectric point. In a preferred embodiment the pH of the cation exchange column is between 6.5 and 8.5, more preferably, the pH is 7.0. The precursor protease is eluted from the column in partially purified form with a gradient of increasing salt concentration.

In one embodiment of this invention, the protease is further purified by hydrophobic interaction chromatography (HIC) after the addition of sodium chloride to 2M and application to the HIC column. Elution from the HIC column is achieved by application of a decreasing salt gradient to the HIC column. The majority of the protease obtained at this stage of purification is precursor protease, although a small amount of mature protease and trace amounts of host proteins may also be present. This mixture, which is essentially free from associated viral proteins forms another aspect of this invention.

The precursor protease is then subjected to autoprocessing conditions which favor its autocatalytic conversion to mature form. One preferred autoprocessing condition includes concentrating the precursor protease to a concentration of at least about 1 mg/ml, although in some instances somewhat lower concentrations will also exhibit autocatalytic activity. Another preferred condition for autoprocessing includes changing the solvent in order to increase the activity of the precursor protease or itself. One such change to the solvent includes the addition of salts. Suitable salts include the potassium, sodium and ammonium salts of: sulfate, citrate, succinate, isocitrate, cis-aconitate, fluoride, and any other anion with multiple charges. A preferred salt is sodium citrate. The concentration of the salt may be between about 0.5M to 2M, more preferably 1M.

After autoprocessing the 32 kDa protein band observed on SDS page gels disappears and two new bands, with apparent molecular masses of 27 kDa and 6 kDa appear.

These proteins may be reintroduced into a HIC column and washed with salt to recover essentially pure 27 kDa protease. The autoprocessing procedure results in a change in elution position of the enzyme on the second HIC step, freeing it from impurities which still elute at the previous position.

Alternatively, in another embodiment of this invention, the precursor protease may be autoprocessed after the first chromatography step (using Fractogel®-SO$_3$). The resulting mature form of the protease is re-chromatographed using Fractogel®-SO$_3$ and elutes at a different position than the precursor protease. The change in elution position allows the separation of the enzyme from impurities which co-elute with the precursor protease.

The N-termini of the 32 kDa protease and its 27 kDa and 6 kDa cleavage product were sequenced and found to be in agreement with the amino acid sequence of FIG. 1 (SEQ. ID. NO.:2) beginning with the Ala at position 2. The N-terminal sequence of the 59 amino acid 6 kDa sequence was found to be consistent with autocleavage between amino acids 247 and 248 of the precursor.

HSV-1 protease has been shown to cleave specific alanineserine bonds in its substrate protein (DiIanni et al., 1993, J. Biol. Chem. 268:2048–2051). Therefore, the cloned and purified protease was tested to determine it it also showed this activity. Peptides having the two known cleavage sites were made and incubated with the purified 27 kDa protein. These peptides were:

His—Thr—Tyr—Leu—Gln—Ala—Ser—Glu—Lys—Phe—Lys—Met—amide (SEQ. ID. NO.:3) and
Ala—Leu—Val—Asn—Ala—Ser—Ser—Ala—Ala—His—Val—Asp—Val—Asp—Thr—Ala—Arg—Ala—Ala—Asp (SEQ. ID. NO.:4).

After incubation with the enzyme, two new peptide peaks were obtained in the HPLC analysis for each substrate incubated with the enzyme. The peptide representing the cleavage site proximal to the N-terminus of the 635 residue HSV-1 protease His-Thr-Tyr-Leu-Gln-Ala-Ser-Glu-Lys-Phe-Lys-Met-amide (SEQ. ID. No.:3) was cleaved by the 27 kDa mature protein at the expected site between the alanine and serine to yield two six amino acid peptides. Likewise, the peptide with the sequence of the cleavage site proximal to the C-terminus of the 635 residue HSV-1 preprotease, Ala-Leu-Val-Asn-Ala-Ser-Ser-Ala-Ala-His-Val-Asp-Val-Asp-Thr-Ala-Arg-Ala-Ala-Asp (SEQ. ID. NO.:4) was cleaved between the Alanine-Serine to yield a five amino acid peptide and a 15 amino acid peptide. The identities of the peptide products were confirmed to be as predicted with amino acid analysis. These products also co-eluted with synthesized peptide product standards. No other cleavage products were observed in the HPLC chromatograms.

While the peptide cleavage reactions observed were consistent with the specificity of HSV-1 protease toward protein substrates, the possibility of a small amount of *E. coli* protease contributing to the reaction needed to be considered. The hydrolytic activity of the partially purified 306-residue precursor with the His-Thr-Tyr-Leu-Gln-Ala-Ser-Glu-Lys-Phe-Lys-Met-amide (SEQ. ID. NO.:3) substrate was found to be 5 nmol/hr/mg and the corresponding value for the mature 246-residue protease was 105 nmol/hr/mg under assay conditions detailed in the Examples. Thus, conversion to the mature form increased the activity of the protease and was unlikely to be due to contaminating bacterial proteases. The fractions from the HIC columns that contained peptide cleavage activity also contained either the 32 kDa protein or the 27 kDa protein. The shift in the elution position of the protease upon conversion of the 32 kDa protein to the 27 kDa form coincided with the shift in elution position of the peak peptide cleavage activity. Therefore, cleavage was not due to bacterial contamination.

The mature protease may be used to identify potential viral protease inhibitors.

This invention may be further illustrated by the following non-limiting Examples.

EXAMPLES

Example 1

Bacterial Growth and Expression

The bacterial expression plasmid coding for the expression of the first 306 amino acids of the HSV ICP35 open reading frame was obtained by polymerase chain reaction with a purified restriction fragment of viral genomic DNA (KOS strain) as a template. Primers were designed on the basis of the HSV-1 strain 17 sequence (McGeoch, D. J. et al., 1988 *J. Gen. Virol.* 69:1531–1574) which is hereby incorporated by reference. The amplification employed 7-deaza-GTP.

The DNA encoding the 306 amino acid fragment was inserted into the NdeI and BamHI sites of the expression vector pET 3C, a known and available vector, described in Studier, et al., 1990 *Methods Enzyomol.* 185:60–89, which uses the T7 promoter. This vector was designated pT7-306. Expression clones were obtained by transformation of BL21(DE3)pLysS cells. Cells were grown at 37° C. in shaker flasks in Luria-Bertani medium with 75 µg/ml ampicillin and 50 µg/ml chloramphenicol to an optical density of 0.5 (600 nm). HSV protease synthesis was induced by the addition of isopropyl-β,D-thiogalacto-pyranoside (IPTG) to 0.4 mM, and incubation continued for 2 hours before harvesting cells by centrifugation.

Example 2

DNA Sequence Determination

Double stranded DNA was denatured with 0.2M NaOH and sequenced with the dideoxy chain termination method and Sequenase v. 2.0 (United States Biochemical, Cleveland, Ohio). Primers were based upon the Glasglow Herpes Simplex Virus-1 strain 17 sequence and were obtained from Midland Certified Reagent Co., Midland, Tex. Compression of products on gel electrophoresis were resolved by the substitution of dGTP with either 7-deaza-dGTP or dITP. All nucleotide assignments were made on the basis of agreement from both strands of DNA. In most cases the assignment was also confirmed with multiple overlaps from different primers.

Example 3

Protein Purification

Initial detection of the expressed HSV protease in both cell lysates and preliminary fractionates was by immunoblot detection of the antigen in sodium dodecylsulfate polyacrylamide electrophoresis (SDS PAGE) gels. Samples were transferred to PVDF membranes and probed with rabbit antisera raised against the peptide Arg-His-Leu-Ser-Pro-Ala-Ser-Arg-Glu-Gly-Ala-Arg-Arg-Leu (SEQ. ID. NO.:5), corresponding to amino acid residues 176-189 in FIG. 1. Antisera was kindly provided by Dr. A. Conley, Merck & Co., Inc. Following the identification of a Coomassie brilliant blue staining band unique to induced cells as the protein of interest, Coomassie brilliant blue staining of SDS gels was used to identify the 306 amino acid precursor in subsequent purification steps.

Cell pellets were suspended in cold 50 mM Tris HCl, pH 7.5 plus 10% glycerol and 1 mM dithiothreitol (DTT). Hen egg white lysozyme was added to a final concentration of 0.1%. Following the viscosity increase accompanying lysis, $MgCl_2$ and DNase (bovine spleen) were added to final concentrations of 5 mM and 0.01%, respectively. After 30 minutes on ice, the lysate was centrifuged 50 minutes at 4° C. and 15,000 rpm in a Sorvall SS34 rotor.

The supernatant from the centrifuged mixture (10 ml) was diluted 5-fold with 25 mM sodium phosphate, pH 7.0, containing 10% glycerol and 1 mM DTT and applied to a 10×100 mm column of E. Merck Fractogel®-$SO_3$ which was equilibrated in the above buffer. All fractionation procedures took place at 4° C. Following a 5 ml wash with equilibration buffer, a gradient to 1M NaCl in equilibration buffer was applied and ten 5 ml fractions were collected. Following analysis of fractions with SDS PAGE (14% acrylamide), the most highly purified fractions were combined with 5 ml of 50 mM TrisHCl, pH 7.5 10% glycerol, 1 mM DTT. NaCl was added to a final concentration of 2M. The sample was applied to a 7.75×100 Baker Hi-propyl HIC column equilibrated with 50 mM Tris-HCl, pH 7.5, 10% glycerol, 2M NaCl, and 1 mM DTT. Following wash with the HIC equilibrium buffer, a gradient from equilibrium buffer to the same buffer without the added NaCl was run (50 ml), and fractions were collected. Fractions containing the majority of the HSV 32 kDa band were pooled, and concentrated on Centricon-10 filters (Amicon, Inc., Beverly, Mass.). The salt concentration of the sample was reduced 5-fold by dilution with HIC buffer lacking NaCl. The final sample was reconcentrated and left for 16 hr at 4° C. for autoprocessing. NaCl was added to a final concentration of 2M and the sample was reapplied and eluted from the Baker HIC column as described above.

Example 4

Protein Purification Using Only Fractogel®-SO$_3$

The protocol in Example 3 was followed except that autoprocessing was induced after the first chromatography step. The first Fractogel®-SO$_3$ column was loaded as in Example 3, and eluted with a linear gradient of 0 to 0.5M sodium citrate. Peak fractions from the elution of the Fractogel®-SO$_3$ were pooled and sodium citrate was added to a final concentration of 0.5M. The sample was allowed to autoprocess for 3 hr at 4° C. The salt concentration was then lowered by passing the sample over PD10 columns (Bio-Rad Inc., Hercules, Calif.) which had been equilibrated in 25 mM sodium phosphate, pH 7.0 containing 10% glycerol, 1 mM EDTA, 1 mM DTT. The desalted sample was applied to a fresh Fractogel®-SO$_3$ column as before, and eluted with a linear gradient of sodium citrate from 0 to 0.5M, and fractions collected. Analysis with Coomassie brilliant blue staining of SDS gels (14% acrylamide), revealed that the fractions containing the peak of the mature HSV protease contained a single 27 kDa band, the HSV protease.

Example 5

Activity Assays

The amino acid sequences surrounding the known cleavage sites of the 635 amino acid precursor (at residues 247/248 and 610/611) were used for the peptide substrates His-Thr-Tyr-Leu-Gln-Ala-Ser-Glu-Lys-Phe-Lys-Met-amide (SEQ. ID. NO.:3) and Ala-Leu-Val-Asn-Ala-Ser-Ser-Ala-Ala-His-Val-Asp-Val-Asp-Thr-Ala-Arg-Ala-Ala-Asp (SEQ. ID. NO.:4). Reactions were initiated by the addition of enzyme aliquots to substrate at 30° C, incubated for the times indicated and quenched by the addition of 5% H$_3$PO$_4$. Separation of cleaved peptides front substrate was achieved by HPLC on either 15 cm or 5 cm Vydac C-18 reverse phase columns with 0.1% H$_3$PO$_4$ and acetonitrile as the aqueous and organic phases, respectively. Routine assays during purification were performed with 4 mg/ml His-Thr-Tyr-Leu-Gln-Ala-Ser-Glu-Lys-Phe-Lys-Met-amide (SEQ. ID. NO.:3) in pH 7.5 Tris HCl, 10% glycerol and 1 mM EDTA for 0.5 to 4 hrs. Additional assays for kinetic characterization of peptide cleavage were performed in a mixture of 52 mM MES, 52 mM TAPSO and 100 mM diethanolamine, pH 7.5 with 25% glycerol, 1 mM EDTA, 1 mM dithiothreitol and 0.1% bovine serum albumin added.

EXAMPLE 6

Amino Acid Compositional and Sequence Analysis

The protein and peptide samples were hydrolyzed with 6N constant boiling HCl in sealed, evacuated vials at 100° C. for 20 hrs. Amino acids were analyzed and quantified on a Beckman 6300 analyzer. N-terminal sequence analysis were performed with Edman degradation on an Applied Biosystems Model 470A gas-phase sequencer equipped with a Model 120A PTH analyzer.

---

What is claimed is:

1. A method for producing Herpes Simplex Virus 1 or 2 protease comprising the steps of:

a) separating precursor viral protease from non-protease constituents of a host cell using cation exchange chromatography; and b) subjecting the separated precursor protease to autoprocessing conditions to obtain mature protease.

2. A method according to claim 1 wherein the cation exchange chromatography uses a column of a tentacle cation exchanger consisting of an insoluble matrix, copolymerized from oligoethyleneglycol, glycidylmethacrylate and pentaerythroldimethacrylate, to which are grafted polymerized chains of acrylamide derivatives that are approximately 15 to 50 units in length.

3. A method according to claim 2 wherein the cation exchange column has a pH between 6.5 and 8.5.

4. A method according to claim 1 wherein the autoprocessing conditions comprise concentrating precursor protease to a concentration of at least about 1 mg/ml.

5. A method according to claim 1 wherein the autoprocessing conditions comprise adding a salt to a concentration of 0.5M to 2M.

6. A method according to claim 5 wherein the salt is selected from the group consisting of the potassium, sodium and ammonium salts of: sulfate, citrate, succinate, isocitrate, cis-aconitate, and fluoride.

7. A method according to claim 6 wherein the salt is sodium citrate.

8. A method according to claim 1, further comprising the step of expressing a precursor protease gene in a host cell culture prior to Step a).

9. A method according to claim 1, further comprising the step of purifying the protease obtained from Step a) using hydrophobic interaction chromatography prior to Step b).

10. A method according to claim 1, further comprising the step of further purifying the mature protease obtained in Step b) by cation exchange chromatography.

11. A method for producing Herpes Simplex Virus 1 or 2 protease comprising the steps of:

a) expressing a precursor viral protease gene in a host cell to obtain precursor viral protease;

b) separating the precursor viral protease from nonprotease host cell constituents using a cation exchange column comprising a tentacle cation exchanger consisting of an insoluble matrix, copolymerized from oligoethyleneglycol, glycidylmethacrylate and pentaerythroldimethacrylate, to which are grafted polymerized chains of acrylamide derivatives that are approximately 15 to 50 units in length;

c) further purifying the precursor protease obtained in b) by hydrophobic interaction chromatography; and d) subjecting the precursor protease to autoprocessing conditions to obtain mature protease.

12. A method according to claim 11 wherein the autoprocessing conditions comprise the addition of sodium citrate to a concentration of 0.5M to 2M.

13. A method of producing Herpes Simplex Virus 1 or 2 protease comprising the steps of:

a) expressing a precursor viral protease gene in a host cell to obtain precursor viral protease;

b) separating the precursor viral protease from nonprotease host cell constituents using a cation exchange column comprising a tentacle cation exchanger consisting of an insoluble matrix, copolymerized from oligoethyleneglycol, glycidylmethacrylate and pentaerythroldimethacrylate, to which are grafted polymerized chains of acrylamide derivatives that are approximately 15 to 50 units in length;

c) subjecting the precursor viral protease to autoprocessing conditions to obtain mature viral protease;

d) purifying the mature viral protease using a cation exchange column as defined in step b).

14. A method according to claim 13 wherein the autoprocessing conditions comprise the addition of sodium citrate to a concentration of 0.5M to 2M.

15. A method according to claim 11 wherein Step a) further comprises transforming a host cell with the precursor protease gene of SEQ. ID. NO.:1.

16. A method according to claim 13 wherein Step a) further comprises transforming a host cell with the precursor protease gene of SEQ. ID. NO.:1.

17. The method of claim 1 wherein the viral protease is Herpes Simplex Virus 2 protease.

* * * * *